United States Patent [19]

Tsou

[11] Patent Number: 5,122,131
[45] Date of Patent: Jun. 16, 1992

[54] ORTHOPAEDIC DEVICE FOR MECHANICAL COUPLING TO A SURGICAL ROD

[76] Inventor: Paul M. Tsou, 526 Adelaide Dr., Santa Monica, Calif. 90402

[21] Appl. No.: 669,651

[22] Filed: Mar. 14, 1991

[51] Int. Cl.⁵ ............................................. A61F 5/02
[52] U.S. Cl. ........................................ 606/61; 606/53
[58] Field of Search ................... 606/53, 60, 61, 64, 606/72, 73

[56] References Cited

U.S. PATENT DOCUMENTS

| | | | |
|---|---|---|---|
| 4,411,259 | 10/1983 | Drummond | 606/61 |
| 4,648,388 | 3/1987 | Steffee | 606/73 X |
| 4,805,602 | 2/1989 | Puno et al. | 606/61 X |
| 5,007,909 | 4/1991 | Rogozinski | 606/61 |

FOREIGN PATENT DOCUMENTS 283373 9/1988 European Pat. Off. .............. 606/73

OTHER PUBLICATIONS

Zimmer Catalog-"Scoliosis and Spinal Instrumentation Systems-Standard Line and Specialty Products", 91 pp. (no date).

Danek Catalog-"TSRH Spinal Implant System", ® 1990 by Danek Medical, Inc., 16 pp.

*Primary Examiner*—Robert A. Hafer
*Assistant Examiner*—Sam Rimell
*Attorney, Agent, or Firm*—B. F. Spencer

[57] ABSTRACT

An orthopaedic device is disclosed for secure mechanical coupling to an elongated surgical rod. The device consists of a T-shaped member having a short, hollow, cylindrical sleeve portion and a threaded rod portion extending perpendicularly midway between the ends of the hollow sleeve portion. The hollow sleeve portion is adapted for slidable positioning over the cylindrical surface of the surgical rod. A narrow slot is provided through the center of the threaded rod portion, bisecting this rod portion, and through the wall of the hollow sleeve portion. The device further includes a block-shaped member having a central cylindrical bore extending between upper and lower surface and at least one U-shaped cutout extending from the middle of one side through the block into the central bore. A longitudinal slot extends between the upper and lower surfaces and from the front surface through the block into the central bore. The T-shaped member, with inserted surgical rod, is adapted for slidable engagement and capture within the cylindrical bore of the block-shaped member. A locking nut, threadably engaged with the bisected, threaded rod portion, applies a force upon the slotted sleeve member to clamp the cylindrical surface of the surgical rod while holding the T-shaped member and clamped surgical rod in a secure, locked position within the block-shaped member.

10 Claims, 1 Drawing Sheet

ORTHOPAEDIC DEVICE FOR MECHANICAL COUPLING TO A SURGICAL ROD

BACKGROUND OF THE INVENTION

The present invention relates to orthopaedic devices, and, in particular, to an orthopaedic device for providing improved mechanical coupling to a longitudinally extending surgical rod.

The use of elongated, cylindrical surgical rods in the treatment of the diseases of the spine, such as scoliosis, kyphosis, and instability, is well-known in the medical arts. Such rods, known as spinal rods, achieve rigid spinal fixation when mechanically coupled to bone anchor attachments or elements. These rods are available in a variety of diameters, lengths and surface characteristics. Certain of these surgical rods are threaded along their length while others are smooth, notched, or ratcheted. One style is provided with a "diamond-cut" or diamond shaped surface over its entire length.

These longitudinally extending surgical rods are used, generally, in pairs placed on the posterior surface of the left and right sides of the lamina of the human spine. Such rods are mechanically secured at selected locations of the vertebrae of the spine by anchor attachments or elements, i.e., hooks or screws.

One example of a widely used anchor attachment member is the conventional orthopaedic hook having a block-shaped head portion, with a central, cylindrical bore therethrough, and a hook portion. The bore of the orthopaedic hook is slidably positioned over the surface of the surgical rod to the selected location for attachment. The hook portion may have a variety of different shapes, lengths and openings for attachment to specific anatomical sites of the vertebra. When the anatomical site has been determined and the hook portion anchored, the conventional orthopaedic hook is locked to the surgical rod either by ratchet or by one or more setscrews located within the block-shaped head portion.

One type of orthopaedic screw, used as an anchor attachment member, has a block-shaped head with cylindrical bore therethrough for slidable positioning over the surface of the surgical rod to the selected anatomical site. The shank and threaded end of this orthopaedic screw extends perpendicularly from the axis of the cylindrical bore. After the threaded end of the screw is mechanically attached, as in vertebra or pelvic fixation, the screw is retained in position on the surgical rod by one or more setscrews in the head of the screw.

Another anchor attachment element known in the medical art is the eyebolt. This element is a short machine screw with a relatively large block head having a cylindrical bore therethrough, the axis of the bore being perpendicular to the axis of the screw. Like the orthopaedic screw, the cylindrical bore of the eyebolt receives the surgical rod enabling the eyebolt to be slidably positioned along the rod. The eyebolt is used together with a hook member provided with a block-shaped head portion having a pair of mutually perpendicular open yoke portions. The head of the eyebolt, with surgical rod therein, is placed within the first of the open yoke portions while the threaded portion of the eyebolt is placed within the second open yoke portion. The first open yoke portion straddles both the head of the eyebolt and the portion of the surgical rod adjacent each side of the head. The second open yoke portion straddles the threaded portion of the eyebolt. An advancing nut on the threaded end of the eyebolt causes a surface portion of the cylindrical surgical rod adjacent each side of the head of the eyebolt to be drawn into physical contact with a portion of the inner surface of the first open yoke member for friction engagement therebetween. In this manner, the hook member is held in a relatively fixed position with respect to the surgical rod.

The conventional orthopaedic devices, with their closed-bore, block-shaped heads, whether hooks or screws, are extremely difficult to install between the selected anatomical sites and the longitudinally extending surgical rod. This difficulty can be appreciated when it is realized that a plurality of spaced-apart anatomical sites are usually necessary to achieve acceptable treatment of spinal deformities and instability. A plurality of anatomical sites necessitate a plurality of orthopaedic coupling devices. An increase in the number of anatomical sites is highly desirable for the simple reason that the load or force upon each such site is reduced, thereby better distributing the force acting upon each selected site as well as the force acting upon each section of the elongated surgical rod to which the orthopaedic device is attached. The necessity of manually manipulating a long surgical rod into the bores of a number of different hooks or screws is a problem of considerable concern.

Recognizing that these surgical implants are installed during open-back surgery, while the patient is under anesthesia, it is important to provide the orthopaedic surgeon with implants that are easily and securely installed without risk of undesired slippage along, or rotation about, the surgical rod. When it becomes necessary to remove an orthopaedic device, whether hook or screw, or to reposition the same, it is important that this procedure be achieved within the shortest time possible and with assurance that the repositioned implant will be maintained in its correct position with security. As the very nature of the surgical operation places the surgical rod under stress, as by resisting deforming forces of the spine, it will be appreciated that secure and rigid attachment of orthopaedic implant devices to the surgical rod is a paramount necessity.

The present invention introduces an orthopaedic device achieving improved mechanical coupling to a cylindrical rod. The device can be readily installed upon, positioned along, repositioned, and removed from the surgical rod with a minimum of manual manipulation. The device consists of separate first and second members designed for mechanical interlocking, one within the other. The first member is T-shaped and includes a short, hollow, cylindrical sleeve portion having upper and lower ends and a threaded rod portion extending perpendicularly from the outer surface thereof midway between the upper and lower ends. The threaded rod portion is bisected by a narrow slot which also extends through the outer surface of the hollow sleeve portion, the narrow slot lying in a plane defined by the axes of the hollow sleeve portion and the threaded rod portion. The hollow sleeve portion of the T-shaped member is adapted for slidably receiving the cylindrical surgical rod, and the bisected, threaded rod is adapted for receiving a locking nut. The diameter of the bisected, threaded rod portion is dimensioned to be less than the outer diameter of the hollow sleeve portion.

The second member is generally block-shaped and includes a centrally located cylindrical bore extending therethrough between upper and lower surfaces. A longitudinal slot extends between the upper and lower surfaces and from the front surface through the block into the central bore. The width of the longitudinal slot is made less than the diameter of the cylindrical bore. The diameter of the cylindrical bore is chosen to slidably receive the hollow cylindrical sleeve portion, and the width of the longitudinal slot is dimensioned to slidably pass the bisected rod portion of the T-shaped member. A U-shaped cutout, extending from the middle of one of the side surfaces of the block member and through the block member into the central bore, provides an open yoke into which the bisected rod portion of the T-shaped member may be placed. A locking nut, threaded upon the bisected, threaded rod portion but not tightened, mechanically interlocks the T-shaped member within the central bore of the block-shaped member while permitting the two interlocked members to be slidably positioned along the surface of the surgical rod. When the interlocked assembly is properly positioned at the selected anatomical site, advancing the locking nut further upon the bisected, threaded rod portion creates a force squeezing the narrow slot of the T-shaped member to clamp the hollow sleeve portion upon the cylindrical surface of the surgical rod while holding the T-shaped member firmly and rigidly within the block-shaped member. The block-shaped member will include an appropriate anchor attachment member for attachment to a selected vertebra.

Accordingly, a principal object of the present invention is to provide an orthopaedic device capable of achieving a more secure and rigid coupling to a cylindrical surgical rod.

Another object is to provide an improved orthopaedic device that is both easier and faster to attach to, position along, or be detached from, a surgical rod during the course of the surgical operation.

A further object is to provide an improved orthopaedic device consisting of two separate and interlocking members for simplifying the procedural steps required to achieve mechanical intercoupling between the orthopaedic device and a surgical rod.

The above objects of and the brief introduction to the present invention will be more fully understood, and further objects and advantages will become more apparent, from a study of the following detailed description in connection with the drawings.

DESCRIPTION OF THE INVENTION

Figure 1A:
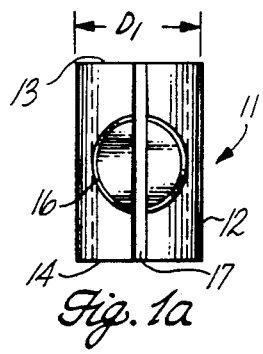
FIGS. 1a, 1b and 1c are enlarged illustrations of the front, side and top views, respectively, of the T-shaped member of the invention.
Figure 1B:
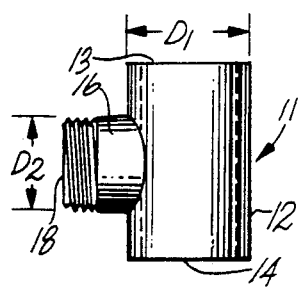
Figure 1C:
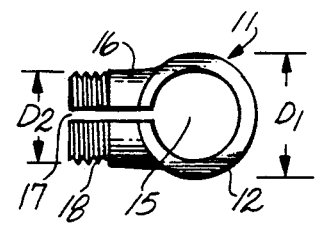

Referring to FIGS. 1a, 1b and 1c of the drawings, the improved orthopaedic device includes a T-shaped member 11 having a first hollow cylindrical sleeve section 12 with upper and lower ends 13, 14 respectively. Hollow cylindrical sleeve section 12 includes bore 15 extending between ends 13 and 14. Bore 15 is dimensioned to slidably receive and pass a longitudinally extending surgical rod.

A second short cylindrical rod section 16, located midway between upper and lower ends 13 and 14, extends perpendicularly from hollow cylindrical sleeve section 12 and is integral therewith, as seen in FIG. 1b. The outer diameter $D_1$ of hollow cylindrical sleeve section 12 is larger than the diameter $D_2$ of cylindrical rod section 16. The diameter $D_2$ of cylindrical rod section 16 is approximately equal to the diameter of the surgical rod for which the orthopaedic device of this invention is to be used.

As can be seen in FIGS. 1a and 1c, a narrow slot 17 extends through the center of cylindrical rod section 16 and through the wall of hollow cylindrical sleeve section 12. Narrow slot 17 extends parallel to the axis of hollow sleeve section 12 from upper surface 13 to lower surface 14 and bisects cylindrical rod section 16. The width of narrow slot 17 is sufficient to permit T-shaped member 11 to be clamped upon the cylindrical surface of the surgical rod when a squeezing force exists between the bisected halves of cylindrical rod section 16, thereby reducing the gap in slot 17.

The squeezing force needed to achieve the desired clamping upon the surgical rod is provided by the threaded end 18 of bisected, cylindrical rod section 16. It is preferred that threaded end 18 be slightly tapered, as in pipe threads, to enable a conventional locking nut engaging threaded end 18 to gradually reduce the gap in slot 17 as the locking nut advances.

Figure 2A:
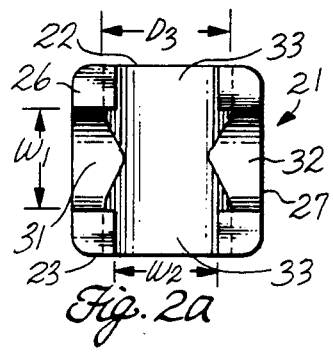
FIGS. 2a, 2b and 2c are enlarged illustrations of the front, side and top views, respectively, of the block-shaped member for slidably receiving the T-shaped member of FIGS. 1a, 1b and 1c.
Figure 2B:
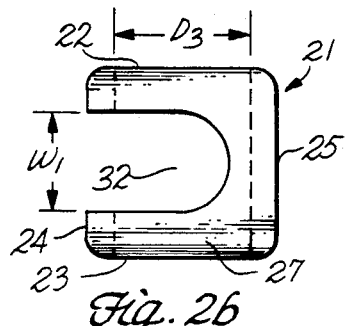
Figure 2C:
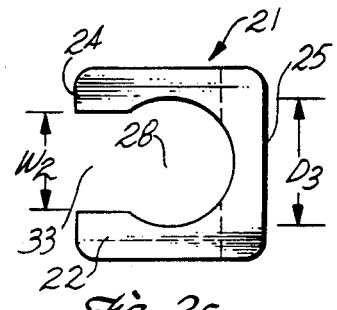

Referring to FIGS. 2a, 2b and 2c, the improved orthopaedic device further includes block-shaped member 21 having upper and lower surfaces 22, 23, front and rear surfaces 24, 25, and having left-side and right-side flat surfaces 26, 27. A cylindrical bore 28 extends through the central portion of block 21 between upper and lower surfaces 22, 23, as best seen in FIG. 2c. The diameter $D_3$ of cylindrical bore 28 is slightly larger than the outer diameter $D_1$ of hollow cylindrical sleeve section 12 of T-shaped member 11, as will be explained hereinbelow.

A U-shaped cutout 31 in the left-side 26 of block member 21 extends from the flat left side through block 21 into central bore 28. Another U-shaped cutout 32 in right-side 27 of block member 21 extends from the flat right side through the block 21 into central bore 28. The open end of U-shaped cutouts 31 and 32 extend to front surface 24, as shown in FIGS. 2a and 2b. The width $W_1$ of U-shaped cutouts 31 and 32 is slightly larger than the diameter $D_2$ of cylindrical rod section 16 of T-shaped member 21, as will be further explained hereinbelow.

A longitudinally extending slot 33 of width $W_2$ extends from front surface 24 through block 21 into central bore 28. Slot 33, parallel to the axis of bore 28, extends between the upper and lower surfaces 22, 23 of block 21, as shown in FIG. 2a. The width $W_2$ of slot 33 is substantially the same as the width $W_1$ of U-shaped cutouts 31 and 32, but is smaller than the diameter $D_3$ of central bore 28, as can be seen in FIG. 2c.

Figure 3:
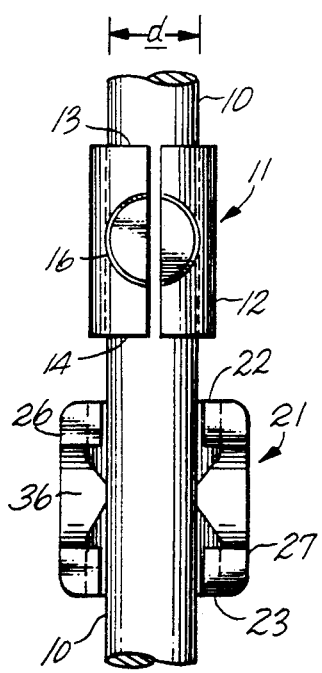
FIG. 3 is a front view of the T-shaped member, with inserted surgical rod, oriented and aligned for slidable insertion into the central bore of the block-shaped member.
Figure 4:
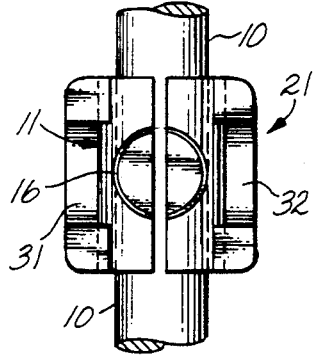
FIG. 4 is a front view of the T-shaped member, with inserted surgical rod, positioned within the central bore of the block-shaped member.
Figure 5:
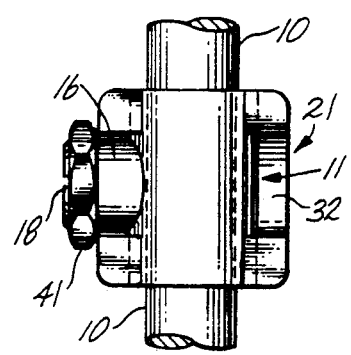
FIG. 5 illustrates the T-shaped member rotated ninety degrees about the axis of the surgical rod, thereby placing the threaded rod portion within the U-shaped cutout of the block-shaped member and locked in this position by a locking nut threadably engaged on the threaded rod portion.

The orthopaedic device of the invention is affixed and clamped to a surgical rod in a manner illustrated in FIGS. 3, 4 and 5. Referring first to FIG. 3, the surgical rod 10, having a diameter d, is shown inserted within the hollow cylindrical sleeve section 12 of T-shaped member 11. Surgical rod 10 is also illustrated as being placed within central bore 28 of block member 21. It will be noted that the diameter d of surgical rod 10 is less than the width $W_2$ of longitudinally extending slot 33, thereby readily allowing surgical rod 10 to be placed within block 21.

T-shaped member 11, when oriented and positioned on surgical rod 10 as shown in FIG. 3, may be slidably positioned over surgical rod 10 in a downward direction for insertion into central bore 28 of block 21. It will be noted that the outer diameter $D_1$ of T-shaped member 11 is slightly less than the diameter $D_3$ of central bore 28 of block member 21, thereby enabling the T-shaped member to be readily slidable into central bore 28. Since the diameter $D_2$ of cylindrical rod section 16 of T-shaped member 11 is slightly less than the width $W_2$ of slot 33, this rod section 16 readily passes through the slot 33.

FIG. 4 shows T-shaped member 11 correctly positioned within bore 28 of block-shaped member 21 in a captive fashion. This important feature of the invention is achieved by virtue of the fact that the longitudinally extending slot 33 of block 21 has a width $W_2$ less than the outer diameter $D_1$ of T-shaped member 11. Accordingly, the surgical rod 10 within T-shaped member 11 is held within block member 21 without the necessity of any additional manual positioning of either block-shaped member 21 or T-shaped member 11.

The final locking and securing of surgical rod 10 and T-shaped member 11 within block member 21 is illustrated in FIG. 5. By the step of manually rotating T-shaped member 11 ninety degrees about the axis of surgical rod 10, the threaded end 18 of bisected rod section 16 will fall within the U-shaped cutout 31 or 32, depending upon the direction of rotation of T-shaped member 11. A locking nut 41, shown threaded upon threaded end 18 of rod section 16 and advanced to bear upon the left-side flat surface 26 of block member 21, applies the squeezing force required to securely clamp surgical rod 10 within T-shaped member 11 while at the same time securing T-shaped member 11 firmly and rigidly within block-shaped member 21.

Figure 6:
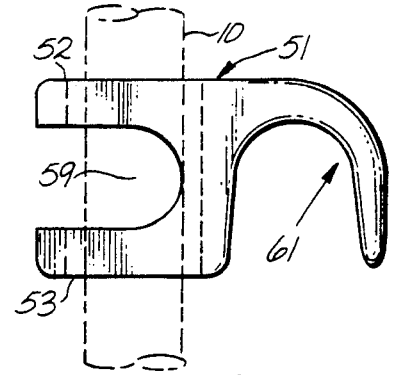
FIG. 6 is a side view of the block-shaped member of FIGS. 2a, 2b and 2c provided with a hook integrally formed on its rear surface.

FIG. 6 illustrates block-shaped member 51 provided with an orthopaedic hook 61 formed as an integral part of the block-shaped member and extending from its rear surface. This embodiment 51 includes upper and lower surfaces 52, 53, a central bore, and a U-shaped cutout 59, in its right-side, in the same general manner as in block-shaped member 21 of FIGS. 2a, 2b and 2c. A surgical rod (shown in broken lines) illustrates the proper alignment of the surgical rod relative to the orientation of hook 61.

It will be appreciated that the length, shape and opening of hook 61 may conform to any of the conventional orthopaedic hooks, such as the open or notched pedicular hook or the laminar hook. Block-shaped member 51 may be coupled to the surgical rod, with hook 61 inverted from the position shown in FIG. 6, when required.

Figure 7:
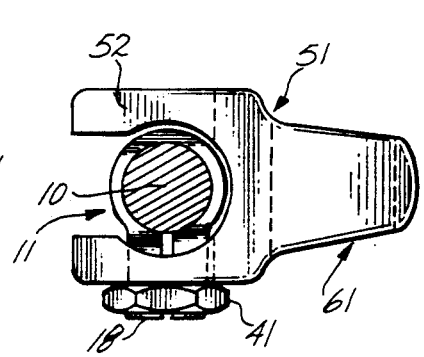
FIG. 7 is a top view of the block-shaped hook member of FIG. 6 secured to a surgical rod by means of the T-shaped member.

FIG. 7 is a top view of the block-shaped embodiment 51 of FIG. 6 used together with T-shaped member 11 and clamped to surgical rod. 10. The manual procedure to secure clamping to the surgical rod is the same as described above in connection with FIGS. 3, 4 and 5. Block-shaped member 51 may be employed on either the left or the right side of the spine of the patient, and T-shaped member 11 may be securely locked within either a U-shaped cutout in the left side of block member 51 or in U-shaped cutout 59 in the right side of block member 51, as illustrated in FIG. 7.

The improved orthopaedic device of the invention is especially suited for clamping to a surgical rod having a smooth cylindrical surface. It is not necessary to employ surgical rods with notched, threaded, knurled or sand-blasted surfaces. The mechanical clamping between the orthopaedic device and a smooth surgical rod has been found to be superior to the mechanical coupling achieved between the known conventional orthopaedic devices and surgical rods. The device may be easily repositioned along the smooth surface of the surgical rod by simply loosening the hexagonal locking nut with a conventional hexagonal wrench, moving the assembly and retightening the locking nut, a procedure frequently required in the standard treatment of the diseases of the spine.

The orthopaedic device may be fabricated of medically approved stainless steel or any other suitable metal approved for medical implants. The physical dimensions of the orthopaedic device are governed, in part, by the diameter of the surgical rod for which the device is to be used. The illustrations appearing in FIGS. 1–7 of the drawing have been drawn to accommodate a surgical rod having a diameter d of one-quarter of an inch, a diameter just slightly larger than six millimeters.

Since many changes may be made in the above-described device and many different embodiments of this invention could be made without departing from the scope thereof, it is intended that all matter contained in the above description or shown in the accompanying drawings shall be interpreted as illustrative and not in a limiting sense.

What is claimed is:

1. An orthopaedic device adapted to be slidably and securely attached to a longitudinally extending cylindrical surgical rod, comprising in combination:

(a) a T-shaped member having a hollow, cylindrical sleeve section with a cylindrical bore extending therethrough, said T-shaped member having a cylindrical rod section extending perpendicularly from said hollow, cylindrical sleeve section, said hollow, cylindrical sleeve section having a first outer diameter, said cylindrical rod section having a second outer diameter less than the first outer diameter of said hollow, cylindrical sleeve section, the bore extending through said hollow, cylindrical sleeve section having a diameter sufficient to receive and pass the longitudinally extending surgical rod;

(b) a first narrow slot extending through the center of said cylindrical rod section bisecting said cylindrical rod section, said first narrow slot extending through a wall portion of said hollow, cylindrical sleeve section into the cylindrical bore, said first narrow slot lying in a plane defined by the axis of said hollow, cylindrical sleeve section and said cylindrical rod section, the axis of said hollow, cylindrical sleeve section being substantially perpendicular to the axis of said bisected cylindrical rod section;

(c) a block-shaped member adapted for slidably receiving said hollow, cylindrical sleeve section of said T-shaped member, said block-shaped member having upper and lower surfaces spaced apart, front and rear surfaces spaced apart, and left and right flat side surfaces spaced apart, said block-shaped member having a centrally located cylindrical bore extending therethrough between said upper and lower surfaces, the cylindrical bore of said block-shaped member having a diameter slightly larger than the outer diameter of said hollow, cylindrical sleeve section of said T-shaped member, said block-shaped member further having a U-shaped cutout extending from one flat side surface of said block-shaped member and through said block-shaped member into said central bore, said U-shaped cutout having a width slightly larger than the outer diameter of said bisected, cylindrical rod section;

(d) a second slot extending through the front surface of said block-shaped member between said upper and lower surfaces and into said central bore, said second slot having a width slightly larger than the outer diameter of said bisected, cylindrical rod section of said T-shaped member, the width of said second slot being less than the outer diameter of said hollow, cylindrical sleeve section of said T-shaped member, said hollow, cylindrical sleeve section of said T-shaped member being slidable within said central bore of said block-shaped member when said bisected cylindrical rod section of said T-shaped member is in alignment with said second slot, said T-shaped member, when positioned within said central bore of said block-shaped member, being angularly positionable about the axis of said central bore when said bisected cylindrical rod section is in alignment with said U-shaped cutout of said block-shaped member; and (e) means adapted to be attached to said bisected cylindrical rod section, when said T-shaped member is positioned within said central bore of said block-shaped member and said bisected cylindrical rod section is positioned within said U-shaped cutout, for applying a force tending to squeeze the bisected cylindrical rod section of said T-shaped member, thereby reducing the gap in said first narrow slot to provide a clamping force upon a surgical rod within said hollow, cylindrical sleeve section of said T-shaped member, said means further appplying a force against said one flat side surface of said block-shaped member for securing said T-shaped member within said block-shaped member.

2. The orthopaedic device as defined by claim 1 wherein the length of said hollow, cylindrical sleeve section of said T-shaped member is substantially equal to the distance between the spaced-apart upper and lower surfaces of said block-shaped member.

3. The orthopaedic device as defined by claim 1 wherein the length of said bisected cylindrical rod section of said T-shaped member is approximately one-third the length of said hollow, cylindrical sleeve section.

4. The orthopaedic device as defined by claim 1 wherein the end portion of said bisected, cylindrical rod section of said T-shaped member, extending perpendicularly from said hollow, cylindrical sleeve section, is threaded.

5. The orthopaedic device as defined by claim 1 wherein the end portion of said bisected, cylindrical rod section of said T-shaped member, extending perpendicularly from said hollow, cylindrical sleeve section, is threaded, and wherein said means adapted to be attached to said bisected, cylindrical rod section, for applying a force tending to squeeze said bisected cylindrical rod section, includes a locking nut.

6. The orthopaedic device as defined by claim 1 wherein said block-shaped member further comprises a second U-shaped cutout extending from the other flat side surface of said block-shaped member, opposite from said one flat side surface, and through said block-shaped member into said central bore.

7. orthopaedic device as defined by claim 1 wherein said block-shaped member further comprises a hook, said hook extending outwardly and downwardly from the rear surface of said block-shaped member, said hook forming an integral part of said block-shaped member.

8. In an orthopaedic device adapted for attachment to the vertebrace of the human spine, the orthopaedic device including a block-shaped member having a slotted, central bore extending therethrough within which a longitudinal surgical rod is to be placed, the block-shaped member for placement around the surgical rod and within the slotted, central bore of the block-shaped member to secure rigid coupling between the surgical rod and the orthopaedic device comprising:

(a) a hollow, cylindrical sleeve member having upper and lower ends, said hollow, cylindrical sleeve member having an outer diameter slightly smaller than the diameter of the central bore of the block-shaped member of said orthopaedic device, said hollow, cylindrical sleeve member being slidably positionable within said central bore, said hollow cylindrical sleeve member having an inner diameter slightly larger than the diameter of the surgical rod, the surgical rod being slidably positionable within said hollow, cylindrical sleeve member;

(b) a short, cylindrical rod member having one end integrally attached to the outer cylindrical surface of said hollow, cylindrical sleeve member midway between said upper and lower ends, said cylindrical rod member extending perpendicularly from the outer cylindrical surface of said cylindrical sleeve member;

(c) a narrow slot extending through the center of said short, cylindrical rod member bisecting said rod member, said narrow slot further extending through the surface of said hollow, cylindrical sleeve member, said narrow slot lying in a plane defined by the axes of said hollow, cylindrical sleeve member and said bisected, cylindrical rod member, said narrow slot defining a gap between the halves of said bisected, cylindrical rod member; and (d) means adapted for attachment to said bisected, cylindrical rod member for applying a force tending to squeeze the halves of said bisected, cylindrical rod member together, thereby reducing the gap in said narrow slot, the force produced by said means being sufficient to cause said hollow, cylindrical sleeve member to clamp the surface of the surgical rod situated therein, said means adapted for attachment to said bisected, cylindrical rod member also applying force between said hollow, cylindrical sleeve member and the block-shaped member of said orthopaedic device when said hollow, cylindrical sleeve member, with inserted surgical rod, is situated within said central bore of the block-shaped member of said orthopaedic device.

9. The combination for placement around the surgical rod within the central bore of the block-shaped member of said orthopaedic device as defined by claim 8 wherein the length of said hollow, cylindrical sleeve member between said upper and lower ends is substantially equal to the length of the central bore extending through the block-shaped member of said orthopaedic device.

10. The combination for placement around the surgical rod and within the central bore of the block-shaped member of said orthopaedic device as defined by claim 8 wherein the other end of said short, bisected, cylindrical rod member is threaded, and wherein said means adapted for attachment to said threaded, bisected, cylindrical rod member for applying a force tending to squeeze the halves of said threaded, bisected rod member together includes a locking nut, said locking nut further applying a force between said hollow, cylindrical sleeve member and the block-shaped member of said orthopaedic device to secure rigid mechanical coupling between the surgical rod and said orthopaedic device.

* * * * *